United States Patent
Falahee (10) Patent No.: US 7,232,463 B2
(45) Date of Patent: Jun. 19, 2007

(54) INTERVERTEBRAL CAGE DESIGNS

(75) Inventor: Mark H. Falahee, Ann Arbor, MI (US)

(73) Assignee: U.S. Spinal Technologies, LLC, Boca Raton, FL (US)

(*) Notice: Subject to any disclaimer, the term of this patent is extended or adjusted under 35 U.S.C. 154(b) by 0 days.

(21) Appl. No.: 10/691,854

(22) Filed: Oct. 23, 2003

(65) Prior Publication Data

US 2004/0126407 A1 Jul. 1, 2004

Related U.S. Application Data

(60) Provisional application No. 60/420,616, filed on Oct. 23, 2002.

(51) Int. Cl.
*A61F 2/44* (2006.01)

(52) U.S. Cl. .................. 623/17.11; 623/17.16

(58) Field of Classification Search ............. 623/17.11, 623/17.16
See application file for complete search history.

(56) References Cited

U.S. PATENT DOCUMENTS

| | | | | |
|---|---|---|---|---|
| 3,867,728 A * | 2/1975 | Stubstad et al. | ......... | 623/17.16 |
| 4,834,757 A * | 5/1989 | Brantigan | ................ | 623/17.11 |
| 4,961,740 A * | 10/1990 | Ray et al. | ...................... | 606/61 |
| 5,055,104 A * | 10/1991 | Ray | ............. | 606/61 |
| 5,192,327 A * | 3/1993 | Brantigan | ................. | 623/17.11 |
| 5,397,364 A * | 3/1995 | Kozak et al. | ............ | 623/17.11 |
| 5,458,638 A * | 10/1995 | Kuslich et al. | .......... | 623/17.11 |
| 5,489,308 A * | 2/1996 | Kuslich et al. | .......... | 623/17.11 |
| 5,609,635 A * | 3/1997 | Michelson | ............... | 623/17.16 |
| 5,683,394 A * | 11/1997 | Rinner | ..................... | 606/86 |
| 5,702,451 A * | 12/1997 | Biedermann et al. | .... | 623/17.16 |
| 5,782,832 A * | 7/1998 | Larsen et al. | ................ | 606/61 |
| 5,980,522 A * | 11/1999 | Koros et al. | ................ | 606/61 |
| 5,984,967 A * | 11/1999 | Zdeblick et al. | ......... | 623/17.16 |
| 6,039,761 A * | 3/2000 | Li et al. | .................. | 623/17.16 |
| 6,086,613 A * | 7/2000 | Camino et al. | .......... | 623/17.16 |
| 6,159,244 A * | 12/2000 | Suddaby | ...................... | 606/61 |
| 6,302,914 B1 * | 10/2001 | Michelson | ............... | 623/17.16 |
| 6,447,548 B1 * | 9/2002 | Ralph et al. | ............. | 623/17.16 |
| 6,607,530 B1 * | 8/2003 | Carl et al. | ..................... | 606/61 |
| 6,613,091 B1 * | 9/2003 | Zdeblick et al. | ......... | 623/17.16 |
| 6,712,852 B1 * | 3/2004 | Chung et al. | ............ | 623/17.11 |
| 6,719,794 B2 * | 4/2004 | Gerber et al. | ............ | 623/17.11 |
| 6,852,129 B2 * | 2/2005 | Gerbec et al. | ........... | 623/17.15 |
| 6,926,737 B2 * | 8/2005 | Jackson | .................... | 623/17.16 |
| 6,953,477 B2 * | 10/2005 | Berry | ....................... | 623/17.11 |
| 6,964,687 B1 * | 11/2005 | Bernard et al. | .......... | 623/17.16 |
| 7,018,416 B2 * | 3/2006 | Hanson et al. | ........... | 623/17.16 |
| 7,044,971 B2 * | 5/2006 | Suddaby | ................... | 623/17.15 |

(Continued)

FOREIGN PATENT DOCUMENTS

WO     WO 01/03615 A1 * 1/2001

*Primary Examiner*—Paul B. Prebilic
(74) *Attorney, Agent, or Firm*—Gifford, Krass, Sprinkle, Anderson & Citkowski, PC (57) ABSTRACT

Cage systems that improve upon the prior art in various ways. In the preferred embodiments, devices are radiolucent, with markers, thereby allowing visualization of placement without excessive obscuration. Devices according to the invention eliminate multiple steps, instruments and trays, while being capable of a custom fit. The devices according to the invention permit easier and greater access to end plate surface area, and can be used with autografts, allografts, and biologics.

14 Claims, 6 Drawing Sheets

U.S. PATENT DOCUMENTS

| | | | |
|---|---|---|---|
| 2002/0052656 A1* | 5/2002 | Michelson | 623/17.11 |
| 2004/0034430 A1* | 2/2004 | Falahee | 623/17.16 |
| 2004/0054412 A1* | 3/2004 | Gerbec et al. | 623/17.15 |
| 2004/0126407 A1* | 7/2004 | Falahee | 424/423 |
| 2005/0143819 A1* | 6/2005 | Falahee | 623/17.11 |

* cited by examiner

Fig - 10B

INTERVERTEBRAL CAGE DESIGNS

REFERENCE TO RELATED APPLICATION

This application claims priority from U.S. Provisional Patent Application Ser. No. 60/420,616, filed Oct. 23, 2002, the entire content of which is incorporated herein by reference.

FIELD OF THE INVENTION

This invention relates generally to spinal implants and, in particular, to improved intervertebral cage designs.

BACKGROUND OF THE INVENTION

There are many intervertebral implants to assist with stabilization and fixation, including pre-assembled mesh rings of varying size; cylindrical threaded cages; carbon fiber boxes; and bone dowels, rings, and wedges. However, all existing devices have certain drawbacks, including the requirement of multiple steps and tools to prepare and mold the intervertebral plates for acceptance of the devices.

Existing implants also exhibit the need to remove/move a distraction device such as a spreader or plugs around a decorticate. Such plugs/distraction devices often get in the way of cage placement. Mesh cages in bone materials can deform or break with attempts to force them into the inner space. Typically, only a small surface of the end plate is exposed to bone graft, this being dictated by the size and position of the cage. Existing devices also require large trays with many instruments and many cages, and it is difficult to see the bone fused in mass inside metal cages, which are radiopaque.

SUMMARY OF THE INVENTION

This invention resides in cage systems that improve upon the prior art in various ways. In the preferred embodiments, devices are radiolucent, with markers, thereby allowing visualization of placement without excessive obscuration. Devices according to the invention eliminate multiple steps, instruments and trays, while being capable of a custom fit. The devices according to the invention permit easier and greater access to end plate surface area, and can be used with autografts, allografts, and biologics.

BRIEF DESCRIPTION OF THE DRAWINGS

FIG. 4A shows how disc material is removed to determine the lateral extent of a disc space;

FIG. 4B is a drawing that shows a disc space being dilated to a desired height using distracters which are preferably color coded;

FIG. 4C shows a cage being inserted;

FIG. 4D illustrates how, with the implant released and the introducer tool removed, easy access is available to the end plates;

FIG. 4E shows how end plates are prepared, and grafting material, biologics, and so forth are packed in;

FIG. 4F shows how an anterior gate is locked into position using the gate holder and locking screws and screwdriver;

FIG. 6D depicts the lower aspect of a cage being locked into a distal vertebrae;

DETAILED DESCRIPTION OF THE INVENTION

Figure 1A:
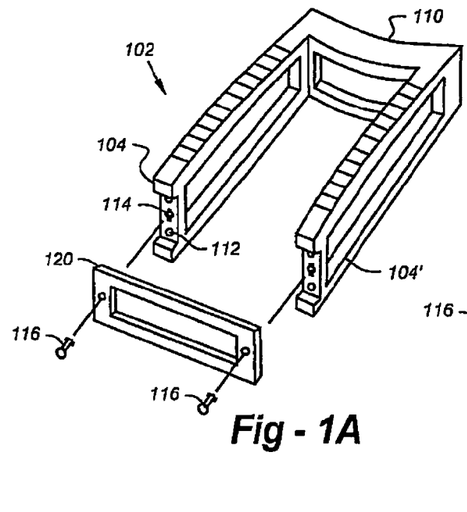
FIG. 1 is a drawing that shows a preferred embodiment of the invention.
Figure 1B:
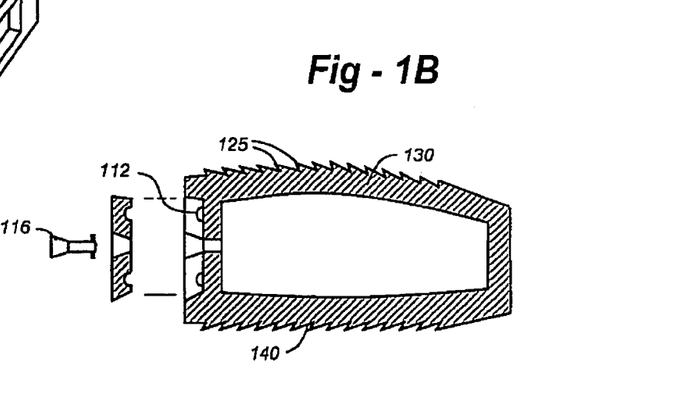
Figure 2A:
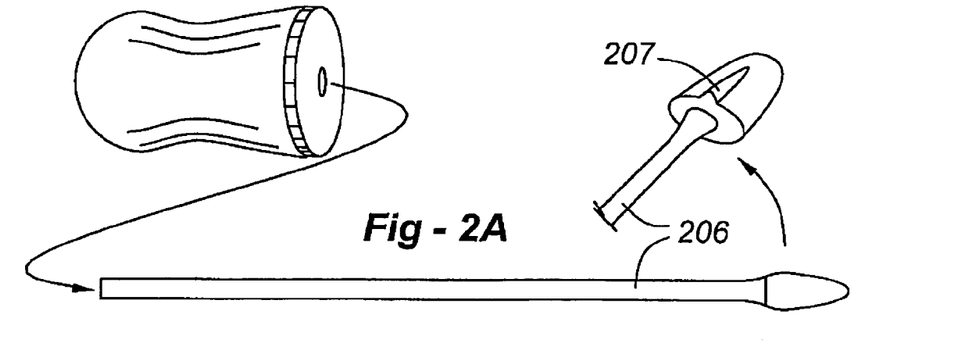
FIG. 2A is a drawing which shows a contoured, wedge-shaped retractor.
Figures 2B, 2C, 2D:
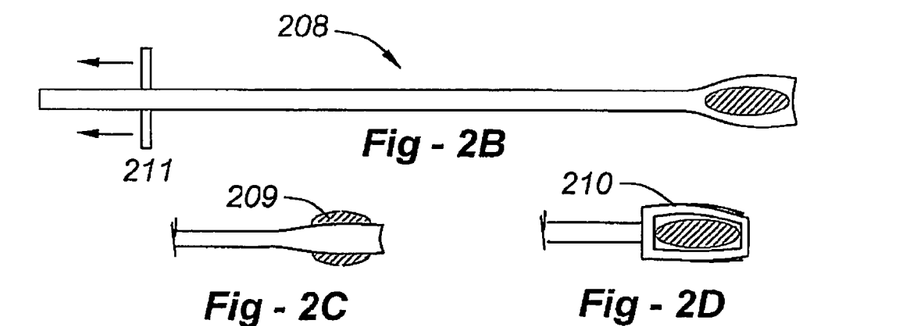
FIG. 2B shows a side view of a U-shaped introducer.
FIG. 2C shows a top view of the U-shaped introducer.
FIG. 2D shows the U-shaped introducer received within a cage.
Figure 2E:
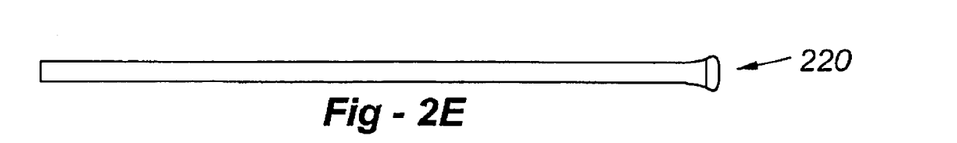
FIG. 2E is a side view of a graft impactor.
Figures 2F, 2G:
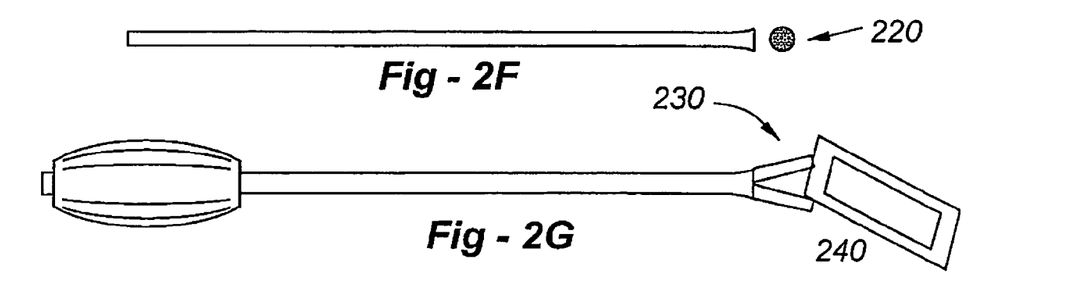
FIG. 2F is a side view of the graft impactor but with an end view of the impactor tip.
FIG. 2G shows a gate holder with a screw mechanism used to capture and release a gate.
Figure 2H:
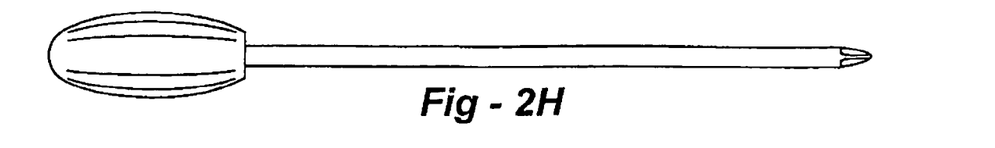
FIG. 2H is a drawing of a screwdriver.

A first preferred embodiment of the invention is depicted in FIG. 1. This design includes an open-faced cage 102, which is constructed of carbon fiber or other radiolucent material but for small dot radiopaque markers (not shown). The device includes a contoured dome-shaped side walls 104, 104' with a flat trapezoidal undersurface. Separate cages and tools may be used for the L5-S1 levels with more pronounced trapezoidal shapes. An indented back wall 110 is used to prevent neurocompression. The side walls preferably include a recessed face with nippled intents 112 and screw holes 114 to receive a locking screw 116. A closing face gate 120 is provided with non-slip nipples and locking screw holes as well.

In addition to the dome-shaped contours of the upper end plate, different shapes for the L5-S1 levels, and the indented back wall, the use of an open-face plate with gate and locking screw mechanism allows the device to be packed and closed in-situ, thereby effectively assembling the cage between the vertebrae. Note that although this design includes numerous features which are believed to be novel, they need not be used entirely in combination, but may be used separately or combined in subsets. The side view at the right in FIG. 1 illustrates the optional use of sawtooth features 125 on the upper surface 130, which is preferably dome-shaped, and the lower surface 140, which is preferably flat.

FIG. 2 is a series of drawings which shows the instruments used to implant devices according to the invention. Most or all are removably attached able to a ratchet handle 200. The set includes a screwdriver 202 (FIG. 2H); contoured, wedge-shaped retractors 206, preferably including a color-coded raised centering mark or ridge 207 (FIG. 2A); U-shaped introducers 208 (FIG. 2B), preferably including retractable wings 209 (FIG. 2C) to release a cage 210 (FIG. 2D) using control 211; graft impactors 220 (FIGS. 2E, 22 and gate holder 230 including a screw mechanism 232 used to capture and release a gate 240 (FIG. 2G). The impactors 230 are generally 25 in length, and preferably come in different sizes, such as 0.8 cm at one end and 1–2 cm at the other, 0.5 cm at one end and 1 cm or less at the other, and so forth.

Figure 3A:
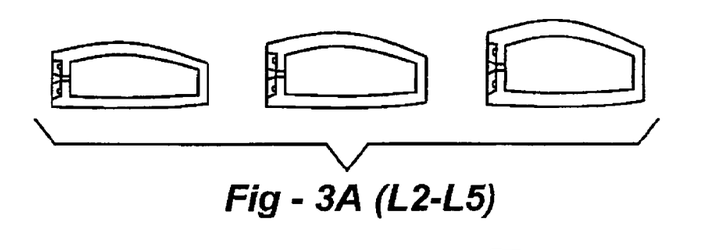
FIG. 3A shows cage shapes for levels L2-L5.
Figure 3B:
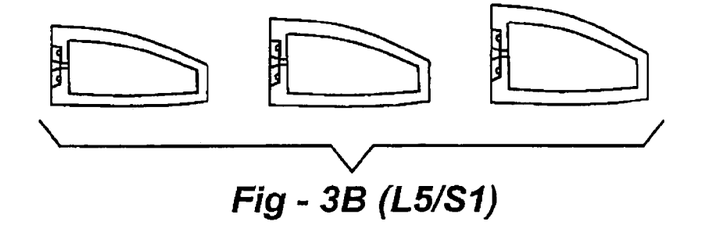
FIG. 3B shows cage shapes for levels L5/S1.
Figure 3C:
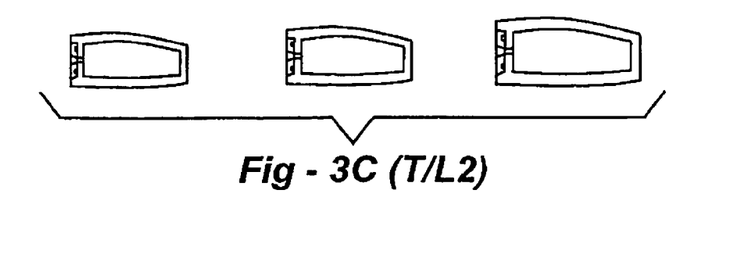
FIG. 3C shows cage shapes for levels T/L2.

FIG. 3 shows how cage shapes would preferably be varied for different vertebral levels. FIG. 3A shows cage shapes for L2-L5; FIG. 3B shows cage shapes for L5/S1; and FIG. 3C shows cage shapes for T/L2. In each case, the implants would preferably utilize some or all of the other geometries described herein, including a general U-shaped construction, crescent-shaped side walls, domed tops, indented back wall, carbon fiber or other radiolucent construction with markers, serrated or tooth-edged, end-plate surfaces, and so forth. The devices would also preferably include correspondingly sized anterior gates, also utilizing carbon fiber or other radiolucent material, with non-slip nipples, locking screw holes and associated screws.

Figures 4A, 4B, 4C, 4D, 4E, 4F:
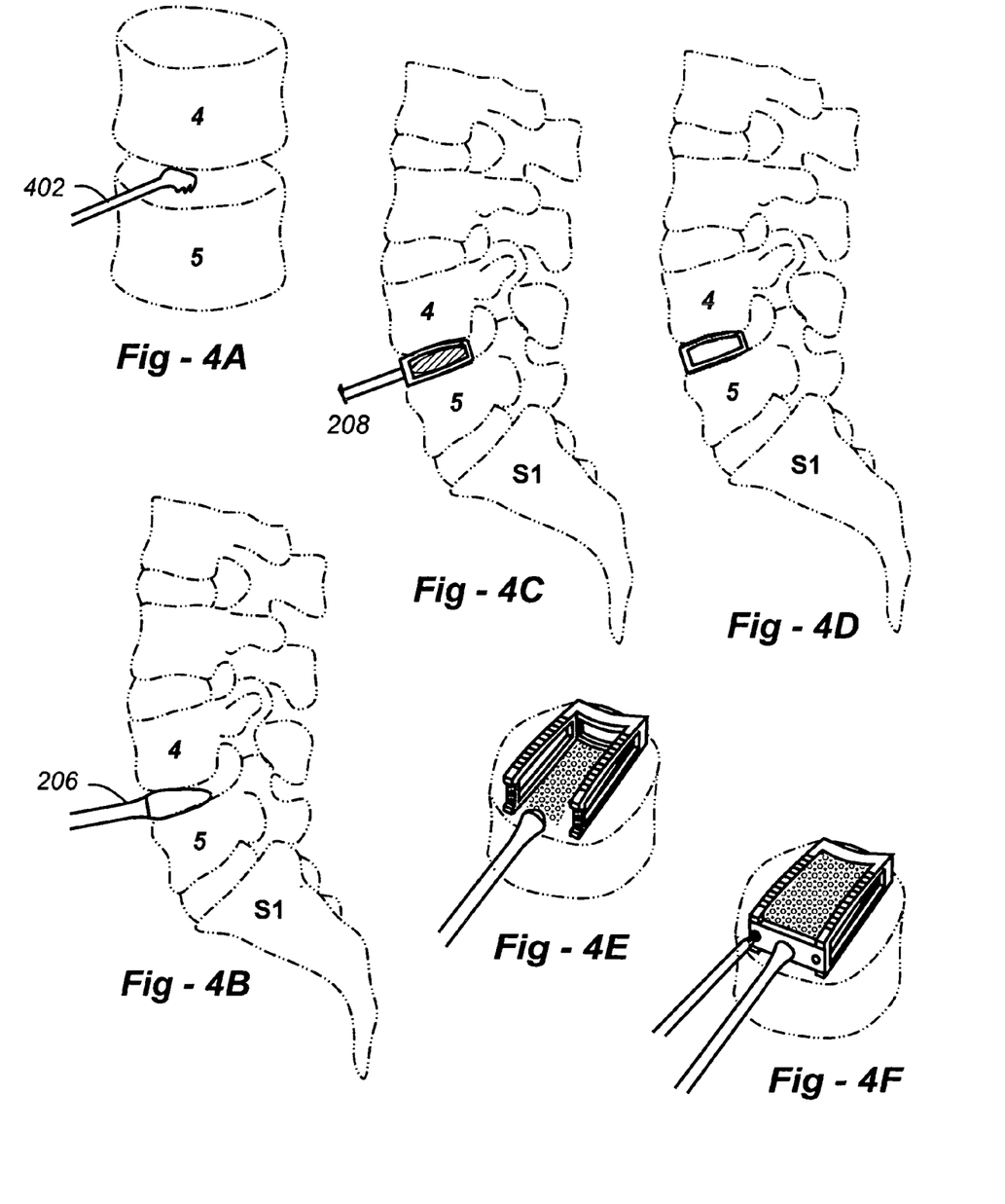

FIG. 4 is a series of drawings which show a method involving an anterior approach to the intervertebral space. In FIG. 4A, disc material is removed with tool 402 to determine the lateral extent of the space. In FIG. 4B, the disc space is dilated to a desired height using distracters 206 which are preferably color coded. The final distracter is removed and replaced with the same color-coded implant introducer instrument 208, with the cage being inserted as shown in FIG. 4C. The implant is released and the introducer tool removed, allowing easy access 410 to the end plates as shown in FIG. 4D.

Figure 5A:
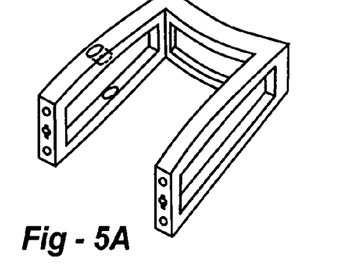
FIG. 5A is a first view of an implant according to the invention.
Figure 5B:
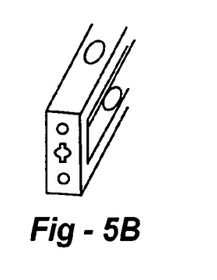
FIG. 5B is a second view of an implant according to the invention.

In FIG. 4E, the end plates are prepared, and grafting material, biologics, and so forth are packed in. In FIG. 4F, a correspondingly sized anterior gate is locked into position using the gate holder and locking screws and screwdriver, and the wound is closed. FIG. 5 begins a series of drawings which shows an alternative embodiment of the invention which allows for an in-situ cage to act as a stand-alone radiolucent cage system. In addition to the instruments previously described, this embodiment utilizes proximal left/right guide sleeves, a drill and universal head screwdriver. In terms of the implant itself, proximal and distal screws are used in conjunction with an in-situ cage having a locking gate, in this case modified to accept proximal screws and guide inferior screws. Different views of the implant are shown in FIGS. 5A and 5B.

Figures 6A, 6C:
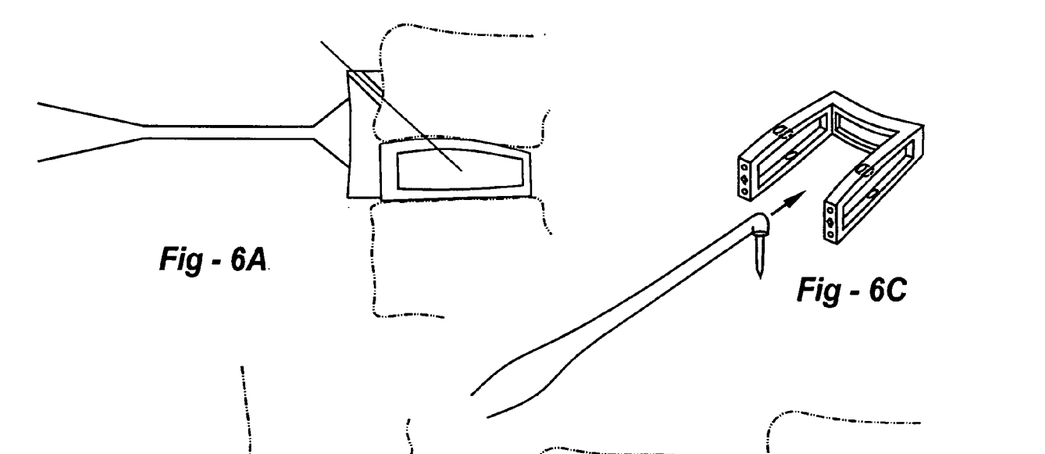
FIG. 6A is a drawing that shows how a proximal guide sleeve is attached onto one vertical side wall of the cage and drilled and tapped as necessary.
FIG. 6C shows how a universal screw driver/holder is used to place distal screws into the cage.
Figure 6B:
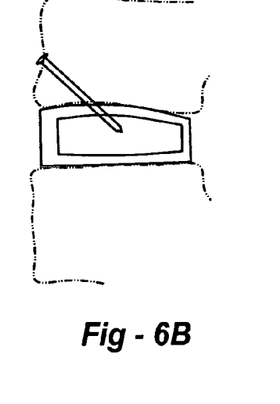
FIG. 6B shows a locking screw in position.
Figure 6E:
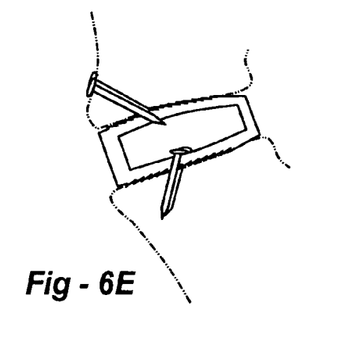
FIG. 6E is a lateral view of a cage in place.
Figure 6F:
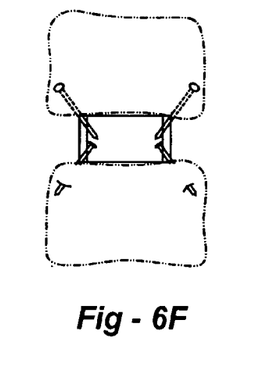
FIG. 6F is an anterior-posterior (AP) view of a cage in place.

In terms of the operative procedure, the steps previously described involving cage insertion are followed. However, in this case, a proximal guide sleeve is attached onto one vertical side wall of the cage and drilled and tapped as necessary, as shown in FIG. 6A. The locking screw is shown in place in FIG. 6B. The universal screw driver/holder is used to place distal screws into the cage, as shown in FIG. 6C, allowing the lower aspect of the cage to be locked into the distal vertebrae as shown in FIG. 6D. FIG. 6E is a lateral view of the cage in place, and FIG. 6F is an A-P view.

Figure 7A:
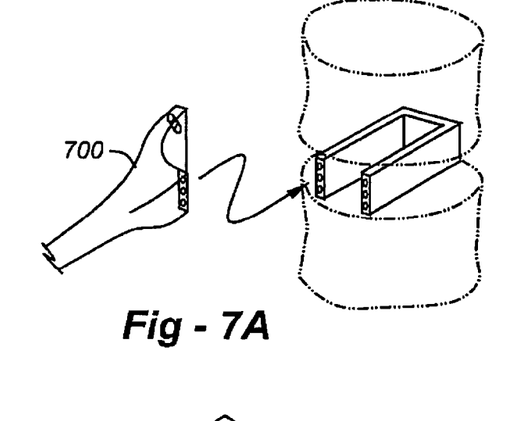
FIG. 7A begins a series of drawings that depict an alternative embodiment of the invention including a different form of anterior fixation.
Figure 7B:
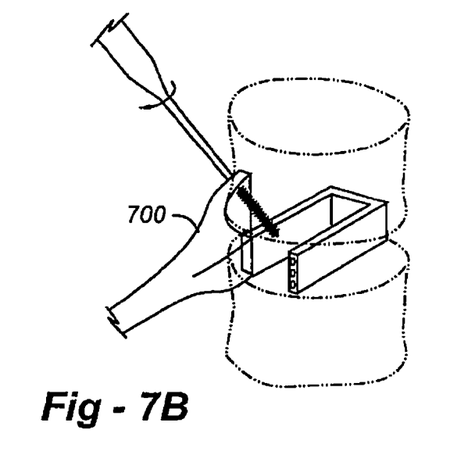
FIG. 7B shows how a fixation jig is used to introduce a screw or similar device through the intervertebral body proximally into the superior cage walls
Figures 7C, 7D, 7E, 8A, 8B, 8C:
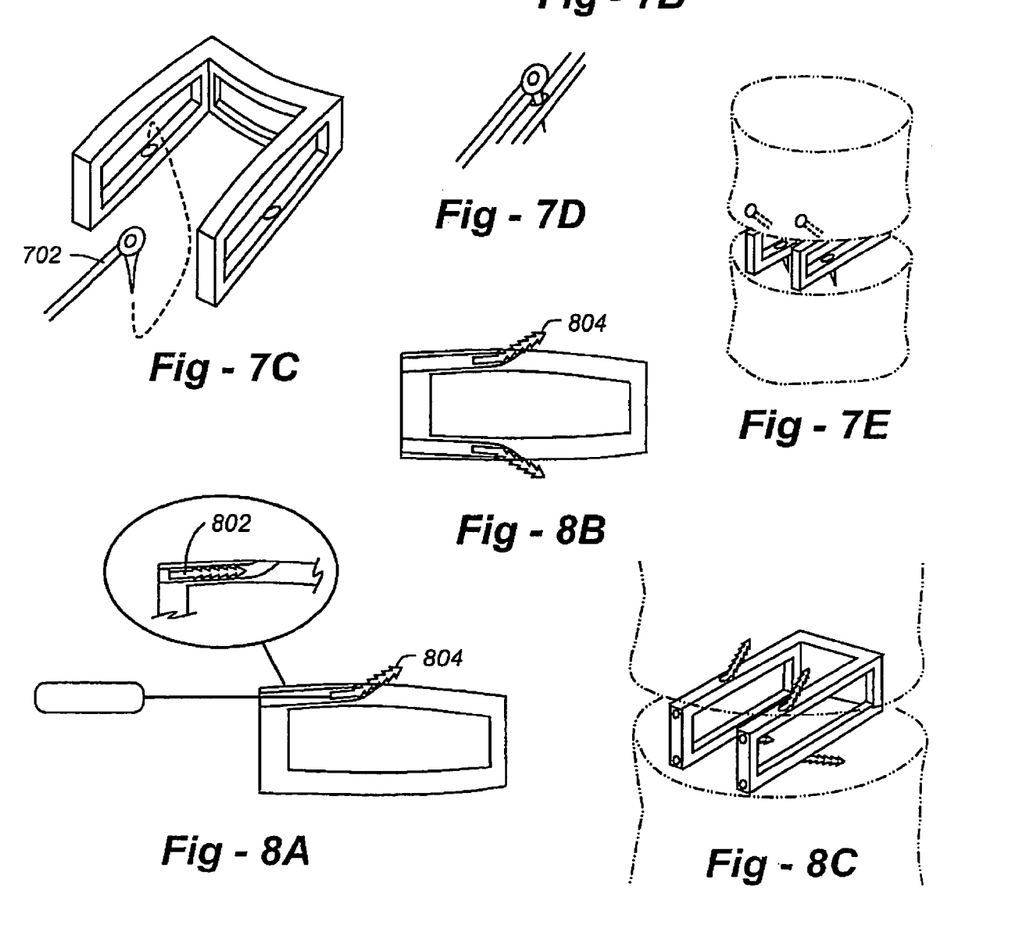
FIG. 7C shows how inferior fixation is accomplished with a ratchet screwdriver/holder to deliver a fastener through the inferior wall of the cage into the vertebral body
FIG. 7D is a drawing that shows how the screw preferably angles out laterally.
FIG. 7E depicts a fixed cage in place.
FIG. 8A shows the anchoring screw being pushed.
FIG. 8B shows the pins advanced.
FIG. 8C shows the device in-situ.

Now turning to FIG. 7 and higher, which depict yet a further alternative embodiment including a different form of anterior fixation. As shown in this case, a fixation jig 700 is used to introduce a screw or similar device through the intervertebral body proximally into the superior cage walls, as shown in FIG. 7B. Inferior fixation is accomplished with a ratchet screwdriver/holder 702, which delivers the fastener through the inferior wall of the cage into the vertebral body as shown in FIG. 7C. The screw preferably angles out laterally, as shown in FIG. 7D, with the fixed cage in place in FIG. 7E. FIG. 8 is a series of drawings which shows internal fixation using an advancing screw to push a fixation pin into the cortical end plate. FIG. 8A shows the anchoring screw 802 being pushed, FIG. 8B shows the pins 804 advanced, and FIG. 8C shows the device in-situ.

Figures 9A, 9B:
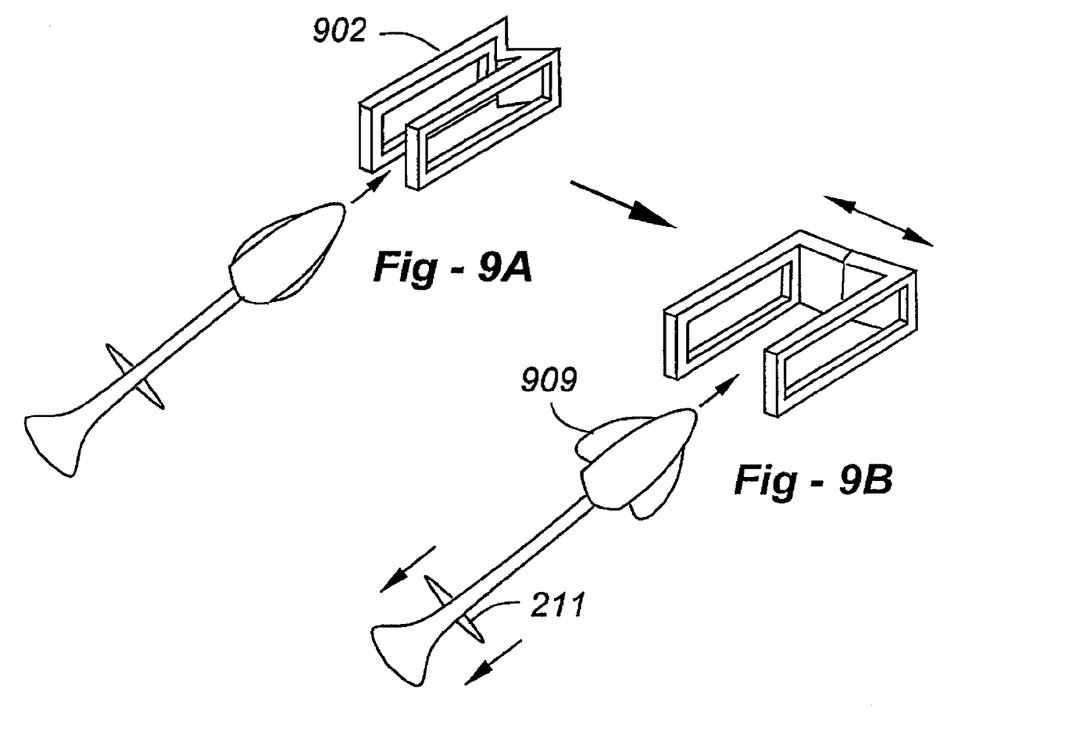
FIG. 9A shows the hinged contoured back wall with the inserter prior to use.
FIG. 9B shows the back wall being straightened and the side walls being spaced apart.
Figure 10A:
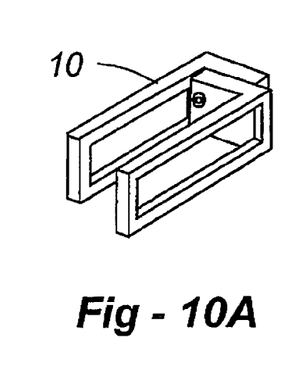
FIG. 10A illustrates a different embodiment involving a sliding lateral expandable cage with locking screws.
Figure 10B:
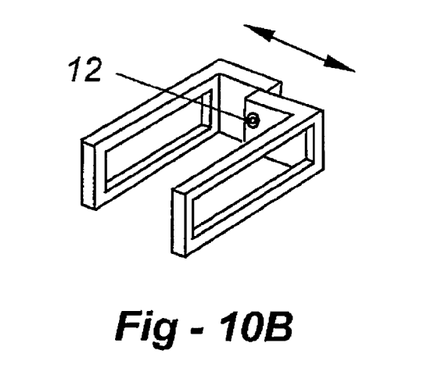
FIG. 10B shows an expanded condition with the locking screws being used to stabilize the structure at a desired level of expansion.

FIG. 9 shows yet a different alternative embodiment of the invention in the form of a collapsing cage suitable for endoscopic placement. The cage is hinged enabling it to be laterally expandable with an expandable cage inserter. FIG. 9A shows the hinged contoured back wall 902 with the inserter prior to use, and FIG. 9B shows the back wall being straightened and the side walls being spaced apart. FIG. 10 shows a different embodiment involving a sliding lateral expandable cage 10 with locking screws 12. Again, an expandable cage inserter is used to move the side walls apart from the condition in FIG. 10A to the expanded condition in FIG. 10B with the locking screw being used to stabilize the structure at a desired level of expansion.

I claim:

1. An implant for promoting intervertebral fusion, comprising:

a cage having two sidewalls, a posterior back wall, an open top, an open bottom, and an open front, such that when viewed from above the sidewalls and back wall form a U-shape;

each sidewall having a convex upper edge and a substantially flat lower edge, such that when viewed from the side, the upper and lower edges conform to outwardly curved and flat planes, respectively, with no portions of the cage extending outwardly beyond either plane;

the front opening allowing the cage to be packed with bone graft and/or biologic materials in situ using an anterior approach; and a physically separate, rigid gate element for closing the open front after the cage is positioned in an intervertebral disc space and packed with bone graft and/or biologic materials.

2. The implant of claim 1, wherein the cage and gate are constructed of a radiolucent material.

3. The implant of claim 1, wherein the cage and gate are constructed of carbon fiber.

4. The implant of claim 1, wherein:
the cage is constructed of a radiolucent material; and
further including one or more radiopaque markers on the cage.

5. The implant of claim 1, wherein the backwall is indented to minimize neurocompression.

6. The implant of claim 1, wherein the backwall is expandable so that the sidewalls can be closer together for insertion and spread apart after implantation.

7. The implant of claim 1, wherein:
the sidewalls have a posterior height and an anterior height; and
wherein the posterior height is less than the anterior height, thereby forming a trapezoid.

8. The implant of claim 7, wherein the anterior height, posterior height, or both, are sized to accommodate a particular vertebral level.

9. The implant of claim 1, further including one or more jigs for fixing the cage in position, including a jig for driving a screw through an upper vertebra into the cage or through the cage into a lower vertebra.

10. The implant of claim 1, wherein:
the backwall has opposing lateral edges; and
wherein each sidewall is rigidly affixed to the backwall at the lateral edges.

11. The implant of claim 1, further including:
an expandable backwall with opposing lateral edges; and
wherein each sidewall is rigidly affixed to the backwall at the lateral edges.

12. The implant of claim 1, further including:
an expandable backwall; and
wherein the sidewalls are generally parallel to one another before and after the expansion of the backwall.

13. The implant of claim 1, wherein:
the sidewalls terminate in anterior edges; and
wherein the gate element extends to each anterior edge.

14. The implant of claim 1, wherein the sidewalls are generally parallel to one another.

* * * * *